US006245038B1

(12) United States Patent
Borberg et al.

(10) Patent No.: US 6,245,038 B1
(45) Date of Patent: Jun. 12, 2001

(54) METHOD FOR TREATMENT OF OPHTHALMOLOGICAL DISEASES

(76) Inventors: Helmut Borberg, Tulpenstr. 19, D51427 Bergisch-Gladbach; Richard Brunner, Im Idienbachtal 28, D-53474 Bad Neuenahr-Ahrweiler, both of (DE)

(*) Notice: Subject to any disclaimer, the term of this patent is extended or adjusted under 35 U.S.C. 154(b) by 0 days.

(21) Appl. No.: 09/000,917

(22) Filed: Dec. 30, 1997

Related U.S. Application Data (60) Provisional application No. 60/034,909, filed on Jan. 7, 1997.

(51) Int. Cl.[7] .............................. A61M 37/00; A61B 19/00
(52) U.S. Cl. ....................... 604/5.01; 604/4.01; 604/5.04; 128/898
(58) Field of Search ................................. 422/44; 604/4; 210/650

(56) References Cited

U.S. PATENT DOCUMENTS

| | | | |
|---|---|---|---|
| 3,727,612 | * 4/1973 | Sayers et al. | 128/214 |
| 3,933,998 | * 1/1976 | Seidehamel et al. | 424/28 |
| 4,103,685 | * 8/1978 | Lupien et al. | 128/214 |
| 4,643,718 | * 2/1987 | Marten | 604/4 |
| 4,830,849 | * 5/1989 | Osterholm | 424/2 |
| 4,900,720 | * 2/1990 | Kotitschke | 514/21 |
| 5,112,298 | * 5/1992 | Prince et al. | 604/6 |
| 5,171,456 | * 12/1992 | Hwang et al. | 210/782 |
| 5,277,820 | * 1/1994 | Ash | 210/646 |
| 5,554,293 | * 9/1996 | Uhoch | 210/650 |
| 5,649,903 | * 7/1997 | Deniega et al. | 604/4 |
| 5,753,227 | * 5/1998 | Strahilevitz | 424/140.1 |

OTHER PUBLICATIONS

Brunner, R.; Erythrocyte apheresis in combination with elimination of fibrinogen and plasma proteins of higher molecular weight in macular disease and in uveal effusion syndrome; Acta Med. Austriaca, 1991, spec Issue 1, 63–65.*

Brunner et al. "Clinical Efficacy of Haemorheological Treatment Using Plasma Exchange, Selective Adsorption and Membrane Differential Filtration in Maculopathy . . . " *Transfus. Sci.* 17(4):493–498, 1996.

Brunner et al. "Change in Hemorrheological and Biochemical Parameters Following Membrane Differential Filtration", *Intl. J. Artifical Organs* 18(12):794–798, 1995.

Brunner, Borberg et al. "Plasma Exchange and Immunoglobulins in the Treatment of Intermediate Uveitis", *Dev. Ophthalmol.*, Karger (Public.) Basel, vol. 23, p. 275–284, 1992.

Brunner, Borberg et al. "Erythrocyte Apheresis in Combination with Elimination of Fibrinogen and Plasma Proteins of Higher Molecular Weight in Macular Disease and in Uveal Effusion Syndrome", *Acta Medica Austriaca 18*, supplement 1, p. 63–65, 1991.

* cited by examiner

*Primary Examiner*—Angela D. Sykes
*Assistant Examiner*—Patricia Bianco
(74) *Attorney, Agent, or Firm*—Needle & Rosenberg, P.C.

(57) ABSTRACT

The invention relates to a method for the effective therapeutic treatment of ocular diseases which comprises the treatment of blood of patients suffering from ocular diseases by extracorporeal plasmapheresis techniques.

3 Claims, 4 Drawing Sheets

METHOD FOR TREATMENT OF OPHTHALMOLOGICAL DISEASES

CROSS-REFERENCE TO RELATED APPLICATION

This application is claiming benefit of a U.S. provisional application Ser. No. 60/034,909; Filing Date: Jan. 7, 1997.

BACKGROUND OF THE INVENTION

The present invention relates to a new method for the effective therapeutic treatment of ocular diseases especially maculopathy and non arteritic anterior ischaemic optic neuropathy (NAION).

In the past ophthalmological diseases like age-related maculopathy (AMD) retinal vein occlusion, diabetic retinopathy, arterial occlusion, uveal effusion syndrome, NAION, Stargardt-disease, uveitis, and maculopathy of different origin could not be treated with a generally accepted therapy. For example for the treatment of AMD lasering treatments, radiation and operation were used. However these methods had no effect on the further development of the disease in many of the patients suffering therefrom. Out of the different ocular diseases AMD is the major disease. AMD is a severe progressive disease which occurs in the elderly. It is considered to be the most frequent cause of blindness in patients beyond an age of 65 years. There are more than 4.5 million Americans suffering from this disease. Two types of AMD are known. The "dry" form develops more slowly, however ends up in blindness generally not later than after 12 to 14 years.

The second form the "wet" type progresses rapidly leading to blindness generally within a few up to 7 years though sometimes much shorter within months. The other ocular diseases which are mentioned above are not so common but also for these diseases no general accepted therapy exists. Therefore, there is a great need for a new and effective therapeutic treatment of the above ocular diseases. In the early '90s the inventors of the present invention observed that the elimination of fibrinogen and plasma proteins of higher molecular weight led to an increase of the visual acuity of patients suffering from macular disease and uveal effusion syndrome (Brunner, Borberg et al. Acta Medica Austriaca 1991, 18, supplement 1, page 63 to 65). In this document 1 patient with uveal effusion syndrome and 16 patients which maculopathy were treated. The haematocrit was reduced by erythrocyte apheresis. Fibrinogen and plasma proteins were eliminated by plasma exchange using a solution of 5% human albumin. The visual acuity of 9 of the patients with maculopathy was significantly increased after one therapy.

In a further publication from 1991 (Brunner, Borberg et al., Dev. Ophthalmol., Karger (Public.) Basel, 1992, vol. 23, p. 275 to 284) it was studied whether clinical improvements could be obtained by plasma exchange therapy with patients suffering from intermediate uveitis using a solution of 5% human albumin. It was found out that both the haemorheological and immunomodulatory effects of this treatment could be beneficial in this disease. Human albumin as well as preserved serum were used as exchange fluids.

However, a general concept for the effective therapeutic treatment of ocular diseases was not described in these documents.

Therefore it was the object of the invention to provide a method for the effective therapeutic treatment of ocular diseases, especially different kinds of maculopathy and NAION.

SUMMARY OF THE INVENTION

This object was solved by a method for the effective therapeutic treatment of ocular diseases which comprises the treatment of blood of patients suffering from ocular diseases by extracorporeal plasmapheresis techniques. According to a preferred embodiment of the invention the ocular diseases which can be treated are selected from the group comprising age-related maculopathy, retinal vein occlusion, diabetic retinopathy, arterial occlusion, uveal effusion syndrome, non arteritic anterior ischaemic optic neuropathy (NAION), Stargardt-disease, uveitis, maculopathy of different origin.

In a further preferred embodiment the plasmapheresis technique is selected from the following techniques: blood cell plasma separation, plasma differential separation, plasma differential precipitation, plasma differential adsorption, plasma differential filtration.

The treatment comprises the steps of withdrawing the blood from the patient, treatment of the blood by the plasmapheresis techniques mentioned above and re-infusing the treated blood.

DETAILED DESCRIPTION OF THE INVENTION

Hemapheresis (apheresis) is defined as the on line separation of blood into blood components. The process of separation refers to the blood cells or to the blood fluid (plasma). Haemapheresis procedures are performed using centrifugal or filtration techniques to modulate blood composition as for instance for the donation of blood components or to perform therapies. The modulation of the blood composition using hemapheresis procedures can generally be attributed to both elimination and dilution. The standard techniques are world wide distributed and under increasing usage.

Rheology is defined as follows. The fluidity of blood as a non Newtonian fluid is characterized from Theological parameters, mainly from viscosity. The viscosity of the blood in the human organism is determined from several variables, the most important being the concentration of blood cells and the protein content of the plasma. Within the plasma high molecular weight proteins, such as low density lipoprotein cholesterol, alpha-2-macroglobulin, immunoglobulin M, fibrinogen, are major determinants. Thus, hyperviscosity syndromes are mainly either due to hypercellularity as it occurs for instance in leukemias or due to an excessively elevated concentration of plasma proteins as for instance in Waldenström's disease. The treatment of diseases characterized from hyperviscosity has for many years been performed using haemapheresis techniques by removing such an excess of cells or plasma. These therapies are also generally known and world wide applied.

Ophthalmological diseases are for unknown reasons hardly or not at all treated with haemapheresis techniques.

Some of them, such as age related macular degeneration are without a generally accepted therapy, though various attempts have without success been made to inhibit the progress of the disease. These failures may be due to a lack of knowledge on the pathogenesis of this and other ophthalmological conditions. Among several hypotheses one of them tries to relate the clinical deterioration with an insufficient and decreasing chorioretinal blood perfusion. Alternatively, an improvement of organ perfusion for instance due to an optimation of blood fluidity could well be used for the treatment of ophthalmological diseases associated with a disorder of the microcirculation.

According to the above mentioned theory it was assumed from the inventors, that a positive clinical effect might be observed in patients suffering from retinal circulatory diseases and many other ophthalmological diseases if the haemorheology could be improved following erythrocyte apheresis in combination with an elimination of fibrinogen and plasma proteins of higher molecular weight. Preliminary observations supported this hypothesis indeed. (R. Brunner, H. Borberg, J. Kadar, M. Heidel, K. Heidner, W. Konen. Erythrocyte apheresis in combination with elimination of fibrinogen and plasma proteins of higher molecular weight in macular disease and uveal effusion syndrome. AMA 1991; 18 (suppl. 1): 63–65). As a correction of the haematocrit is not often necessary, the studies concentrated more on an optimation of plasma viscosity applying plasma exchange against 5% human albumin (R. Brunner, H. Borberg, J. Kadar, A. Hoffmann, W. Konen, M. Heidel, K. Heidner, in Intermediate Uveitis, WRF Böke, K. F. Manthey, R. B. Nussenblatt (eds), Dev. Ophthalmol, Karger (publ.), Basel 1992; 23: 275–284.

Subsequently, several plasma differential separation techniques were investigated and compared with plasma exchange therapy. It could be shown, that plasma viscosity, standardized whole blood viscosity at an hct of 0.45 and standardized erythrocyte aggregation at an hct of 0.30 were still significantly decreased one day after therapy. The values of the standardized whole blood viscosity showed a non-linear, haematocrit-dependent rise, whereas the erythrocyte aggregation revealed the maximum value near a haematocrit of 0.3. A reduction in all adjusted haematocrits was demonstrated. Also, native whole blood viscosity and erythrocyte aggregation were lowered within the same range while the haematocrit was only slightly diminished. The high molecular weight substances of the plasma (Lipids such as total cholesterol, LDL-cholesterol, HDL-cholesterol, proteins such as alpha-2-macroglobulin, immunoglobulin including fibrinogen) were decreased between 20–70% (R. Brunner, R. A. Widder, P. Walter, H. Borberg, K. Oette. Change in haemorheological and biochemical parameters following membrane differential separation. Int. J. Artif.Organs 1995: 18, 12:794–798).

Finally, several plasma differential separation techniques were examined from the inventors to improve the techniques applicable for an extracorporeal haemorheotherapy of ophthalmological diseases.

Techniques applicable for the use within the invention consist of blood cell—plasma separation, also named primary separation, plasma differential separation, also named secondary separation. After the process of separation and elimination of either cells (if necessary) and/or plasma proteins whole blood is returned to the patient. However, these techniques are not obligatory, as whole blood perfusion of filters or adsorbers may also be applied Blood Cell—Plasma Separation (Primary Separation)

Centrifugal separation based on continuous or discontinuous flow principles (e.g. IBM model 2997, COBE Spectra, FRESENIUS AS 104, DIDECO Excel, HAEMONETICS model 50), can successfully be applied to separate blood cells from blood plasma. Alternatively flat sheet membrane (COBE TPE) or hollow fiber plasma separators (ASAHI OP-05) were and can be used to obtain cell free plasma. The separated plasma is discarded to be substituted with human albumin, a mixture or combination of human albumin with other fluids or other fluid alone (plasmaexchange therapy).

For anticoagulation usually heparin, citrate or a combination of both may be applied. Other upcoming anticoagulation procedures are equally applicable. The access to the circulation can be established on a veno-venous basis from one antecubital vein to the other or from a central venous access to a peripheral vein or using an artificial access to the circulation applying for instance a shunt, a Shaldon catheter or any other catheter using for instance Seldinger's technique. Single needle techniques may also be used.

Plasma Differential Separation (Secondary Separation)

As plasma exchange therapy may be characterized from safety drawbacks as for instance the transfer of infectious agents such as viruses or prions, secondary or plasma differential separation techniques are preferred. They consist of plasma differential precipitation with heparin, adsorption or absorption of plasma proteins or plasma filtration. All technologies for secondary plasma separation are preferably applied on-line.

Plasma Differential Precipitation

Plasma differential separation is performed adding an excess of heparin to the separated plasma, establishing a $p_H$ of 5.12 to precipitate heparin binding plasma proteins, separating the precipitate from the plasma by hollow fiber filtration, and removing the heparin excess via adsorption. Any other plasma protein precipitating technique may also be applied.

Plasma Differential Adsorption

Plasma differential separation is performed permitting the separated plasma to pass through an adsorption column eliminating plasma proteins for instance using hydrophobic interaction chromatography (applying for instance an ASAHI TR 350 adsorption column) or affinity chromatography (applying for instance an LDL-apheresis column) or any other related adsorption technology. (As mentioned above, instead of perfusing adsorption columns with separated plasma, whole blood perfusion in biocompatible systems may also be applied).

Plasma Differential Filtration

Plasma differential separation is performed permitting the separated plasma to pass through a secondary filter eliminating plasma proteins according to the pore size of the membranes (for example ASAHI AC 1730, ASAHI AC 1760, ASAHI Rheofilter 2000, ASAHI AC 1770, KURARAY Evaflux filters with different pore sizes, DIDECO Albusave).

Retransfusion

If whole blood perfusion is used, the blood cleared from the eliminated components is returned to the patients. If plasma differential separation is used, the blood components without the cells and/or plasma are returned to the patient.

Figure 1:
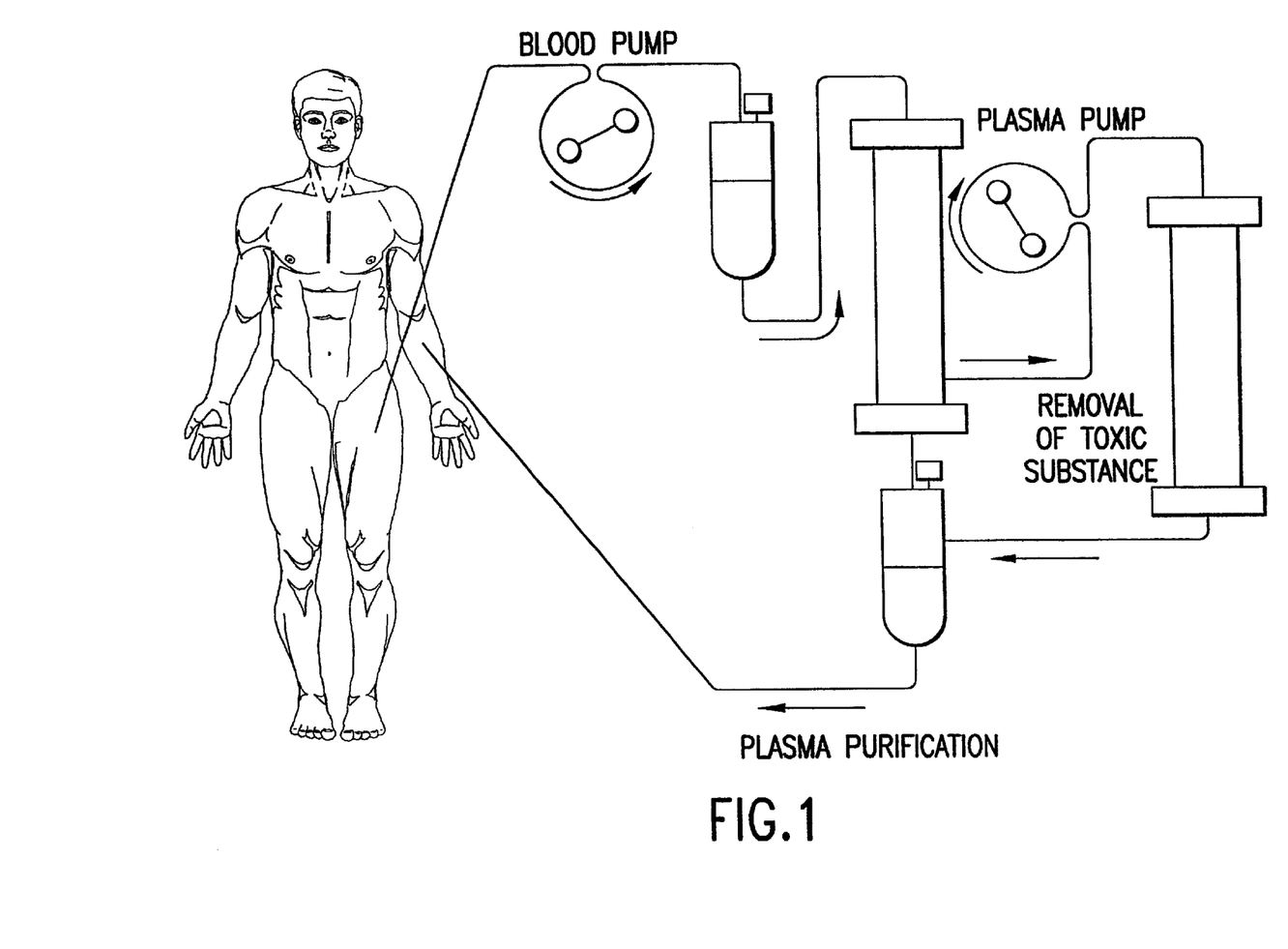
FIG. 1 is a schematic drawing of a patient connected to an extracorporeal system for plasmapheresis.

A typical example of plasma differential separation using filtration as an example is shown in FIG. 1. (Step 1: Blood is removed from a pump into the extracorporeal circuit, where cells are separated from the plasma in a plasma separator. The plasma separator may consist of either a centrifugal or a filtration apparatus. Step 2: The separated plasma is either discarded and replaced (plasma exchange), or, alternatively, permitted to pass through one or more secondary devices eliminating the precipitated, adsorbed or filtered plasma. Step 3: The purified blood is returned to the patient. Note that whole blood perfusion devices are correspondingly simpler)

Treatments were performed processing about 50 to 200% of the patient's plasma volume preferably 120% on day one and about 50 to 150% preferably 60–80% of the patient's plasma volume on day 3 or 4 with either technique described above. Blood samples were drawn prior to and one day after the second treatment to measure the efficacy parameters. Two treatments were considered as one cycle. The interval from one cycle to another was generally 4–5 weeks. A total of 5 treatment cycles was applied.

Other treatment approaches mainly but not only used for maintenance therapy consisted of a single treatment or one single treatment at different intervals. The definition of the interval is related to the choice of the separation techniques, thus other approaches are equally possible.

Patients which were treated with a method according to the invention reported about daily life improvements like improved reading ability, less problems when watching television, better phase recognition, reduction of distorted vision, enhanced color vision perception, and an increased degree of independence.

The present invention will be further understood by reference to the following examples.

EXAMPLE 1

Treatment of patients with age related maculopathy (n=17), uveitis associated (n=14), myopia associated maculopathy (n=5), uveal effusion syndrome (n=3), central retinal vein occlusion (n=4).

To determine the clinical efficiency of haemorheological therapy using plasma exchange, selective adsorption and cascade filtration patients suffering from maculopathy, retinal vein occlusion and uveal effusion syndrome were treated.

36 patients suffering from maculopathies of different origin were treated age related age related (n=17, 31 eyes), uveitis associated (n=14, 26 eyes) and myopia associated (n=5, 9 eyes). Also patients suffering from central retinal vein occlusion (n=4, 5 eyes) resistant to conventional haemodilution and uveal effusion syndrome (n=3, 4 eyes) not responding to steroid application were treated. The mean age of the patients was 58 years (SD 15). The main clinical parameter was the best corrected visual acuity, measured by Early Treatment Diabetic Retinopathy Study charts (Lighthouse New York).

For patients with maculopathy treatment consisted of two treatment sessions with a one day interval. The patients were hospitalized for 5 days. Measurements were carried out one day prior to the first treatment session and 24 hours after the second treatment session. Patients suffering from uveal effusion syndrome and retinal vein occlusion underwent a mean of 3.4 (range 1 to 7) repetitive treatments.

We applied the following extracorporeal treatment procedures: plasma exchange with 5% human albumin solution, selective adsorption using the trytophan-polyvinylalcohol adsorber TR-350 (Asahi Medical Tokyo) and membrane differential separation with the Cascadeflo AC-1760 (Asahi Medical Tokyo). The amount of plasma volume perfused varied between 80–120% of the patient's plasma volume. A centrifugal blood separator (IBM 2997, Cobe Spectra) and the OP-05 hollow fiber filter (Asahi Medical Tokyo) were used for primary separation. The blood flow was established between two antecubital veins. Anticoagulation consisted of heparin (2500 units) injected as a bolus prior to therapy and ACD-A citrate continuously infused at a ratio of 1:16 during the course of treatment. Patients with severe systemic diseases like malignomas, cardial decompensation, hepatitis, HIV infection as well as severe hypotony were excluded. Plasma and standardized, whole blood viscosity at a haematocrit of 45% were measured using a cone-plate system (CS-Rheometer Carri Med Ltd., Dorking, UK) at 37 degrees Celsius and standardized erythrocyte aggregation at a haematocrit of 30% was measured applying the Mini-Aggregometer (Myrenne GmbH, Roetgen, Germany) (7). Measurements of the pulsatile ocular blood flow according to Langham were performed in 10 patients suffering from age related maculopathy (8). For statistical evaluation the Wilcoxon signed rank test was used. P<0.05 was regarded as statistically significant.

Results

Severe side effects did not occur. Five patients showed anticoagulation dependent symptoms of hypocalcaemia such as tingling of the finger tips and the lips and received oral calcium. Three other patients experienced hypotonic episodes with a drop of blood pressure not below 90/60 mmHg. They were treated with the substitution of 250 ml 5% human albumin. No further medical treatment was required.

Maculopathy

Figure 2:
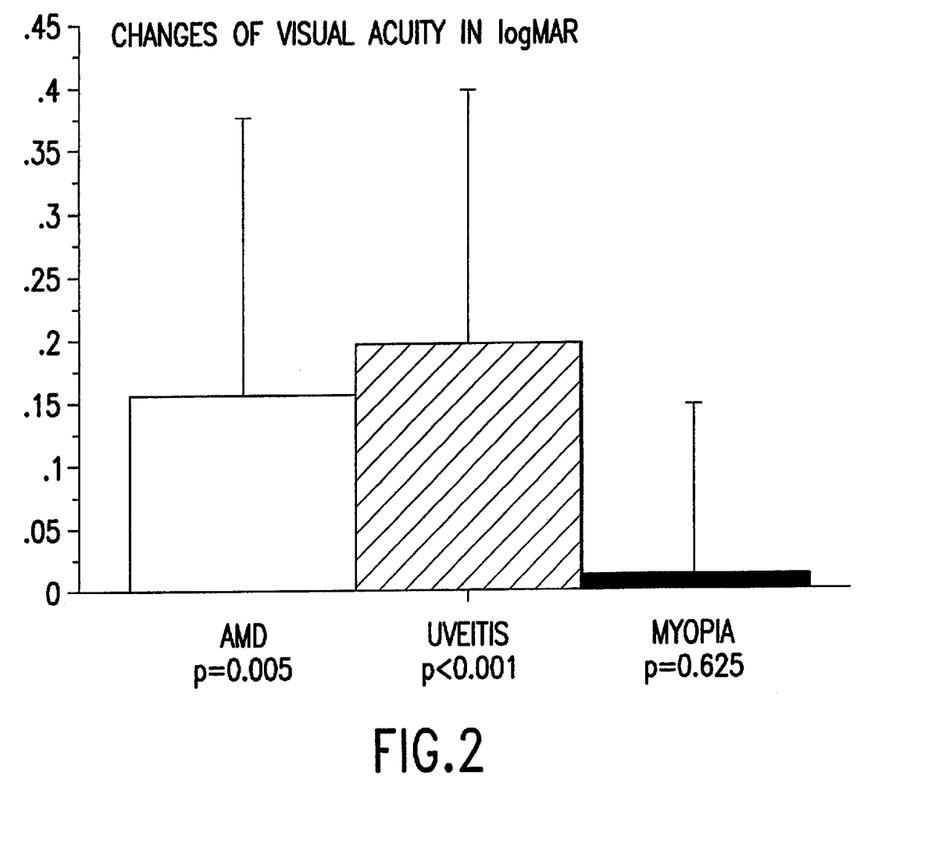
FIG. 2 shows the changes of visual acuity after therapy in patients suffering from maculopathy.

25/36 patients (34/66 eyes) showed an improvement of visual acuity after therapy of at least one line. This improvement was achieved in AMD for 11/17 patients (15/31 eyes), in uveitis for 12/14 patients (17/26 eyes), in myopia for 2/5 patients (3/9 eyes). A bisection of the visual angle (improvement of three lines or more) was achieved in 7/17 patients (age related, 9/31 eyes), 6/14 patients (inflammatory associated, 9/26 eyes) and in 0/5 patients (myopia associated). The changes in visual acuity were statistically significant in AMD and uveitis (FIG. 2). The haemorheological parameters were, significantly lowered: plasma viscosity to 86% (p<0.001), whole blood viscosity to 87% (p<0.001) and erythrocyte aggregation to 65% (p<0.001) of their initial value. The pulsatile ocular blood flow was increased in 9/10 patients. The mean improvement was from 649 (SD 188) before to 790 microliter/minute (SD 250) after treatment (p=0.028). Also the improvement of the pulsatile ocular blood flow as well as the improvement of retinal circulation time after elimination of high molecular weight proteins and lipids were demonstrated.

Retinal Vein Occlusion and Uveal Effusion Syndrome

All patients suffering from retinal vein occlusion showed an improvement of visual acuity of at least one line. In two patients a bisection of the visual angle was achieved. One patient improved his visual acuity from 0.1 to 0.5, a second from 0.0625 to 0.5. All patients with uveal effusion syndrome showed a bisection of the visual angle in all eyes after multiple treatments.

Discussion

Extracorporeal haemorheological treatment led to clinical improvement in 25/36 patients suffering from maculopathy and in all patients with retinal vein occlusion and uveal effusion syndrome. These changes were achieved by optimizing rheological parameters such as plasma viscosity, whole blood viscosity and erythrocyte aggregation. Serious side effects did not occur.

Measuring the pulsatile ocular blood flow, it could be demonstrated that changes of blood viscosity and erythrocyte aggregation led to a modification of the blood supply in the ocular compartment.

Comparing the outcome of the patients with maculopathy the main improvement was achieved treating age related maculopathy and inflammation associated maculopathy while myopia related maculopathy did not display a clinically relevant improvement. The pathogenesis of maculopathy is not fully understood. In age related and inflammation associated maculopathy as well as in retinal vein occlusion a disturbance of the ocular blood flow was found in several investigations. The treatment of choice for uveitis without specific pathogenesis is immunosuppression, e.g. with steroids. Patients in this study developed maculopathy which did not respond to earlier drug therapy. So far age related maculopathy remains without generally accepted or established therapy. Alternative therapeutic strategies are laser coagulation, radiation therapy and subretinal membrane peeling. These approaches are able to slow down the progress or to avoid further complications of the disease. They however fail to improve symptoms such as reduced visual acuity. They additionally have in common the destruction of retinal tissue and are only suitable for a minority of patients.

Uveal effusion syndrome is caused by a decreased blood flow in the vortex veins on their way through the sclera out of the ocular globe. Alternative treatment means surgical decompression with the potential risks of surgery and additional therapy with steroids to which our patients did not respond. In retinal vein occlusion the therapy of choice is the rheological therapy using haemodilution. The benefical effects for the majority of patients were demonstrated in randomized studies. We treated patients who did not respond to this therapy but to extracorporeal treatment. This may be due to the limitations of conventional haemodilution in influencing plasma viscosity. Using hyper- or isovolemic haemodilution an evident or lasting influence on plasma viscosity could not be demonstrated. The effects remained limited to the time interval between the end of treatment and the measurements performed after therapy. Subsequent changes were not detectable 24 hours later. Long term effects have been described but the results remained within the ranges of shamprocedures. Extracorporeal therapy failed to improve visual acuity in myopia related disease. In these patients it seems that the mechanical component, caused by the elongation of the ocular globe, is of major importance. It was not possible to improve visual acuity by improving ocular blood supply.

Rheological treatment is not a causative treatment but it decreases the patient's symptoms by improving the ocular blood supply. Based on the current experience it will be necessary to select those patients who may benefit from therapy through clinical, morphological and electrophysiological criteria.

In patients with uveitis associated maculopathy and retinal vein occlusion an extracorporeal therapy should be carried out after conventional therapy such as steroid treatment or haemodilution have failed.

In age related maculopathy and uveal effusion syndrome extracorporeal treatment should be taken into consideration before invasive techniques are applied. This excludes patients with subretinal neovascular membranes fulfilling the guidelines for laser coagulation of the Macular Coagulation Study Group. In these patients it remains to be elaborated whether extracorporeal treatment prior to laser'therapy is more beneficial.

Extracorporeal treatment procedures like plasma exchange, selective adsorption and cascade filtration are able to improve visual acuity in patients suffering from maculopathy, retinal vein occlusion and uveal effusion syndrome by optimizing rheological parameters. They are able to affect the disease process without causing tissue damage as occuring after laser coagulation, radiation therapy or surgery.

FIG. 2 shows the changes of visual acuity after therapy in patients suffering from maculopathy.

0.1 log MAR unit is equivalent to one line on the used visual acuity charts. Statistically significant changes occurred in patients suffering from age related maculopathy (AMD) and uveitis associated maculopathy. In myopia no clinically relevant changes were detected.

[also see Brunner et Borberg, Transfus, Sci., Vol. 17, No. 4, pp, 493–498, 1996 (published 1997)]. This document is incorporated by Reference.

EXAMPLE 2

Improvement of visual acuity in patients suffering from diabetic retinopathy after membrane differential filtration.

Six patients (4 men and 2 woman) with non proliferative diabetic retinopathy and clinically significant macular edema (5 patients, 9 eyes) according to the definition of the Early Treatment Diabetic Retinopathy Study (ETDRS 1991) and inactive proliferative diabetic retinopathy (1 patient, 1 eye) underwent treatment. The mean age was 61 years (range 56–68 years). Two patients were insulin dependent. The mean duration of the disease was 12 years (range 1 –24 years). One patient showed in one eye no signs of diabetic retinopathy, another patient had 1 eye inoculated after a penetrating injury. So 6 patients (10 eyes) were included into analysis.

A plasmaflo OP-05 hollow fiber filter was used for primary plasma separation. Plasma differential filtration was performed applying the cascadeflo AC 1730 filter (Asahi Medical Tokyo). The blood flow was established by venipuncture of both forearms. Anticoagulation consisted of heparin (4500 units) administered as a bolus prior to treatment and ACD-A citrate (Acidium citrium dextrose formule A) infused during treatment at a ratio of 1:16. 80% of the patients plasma volume was processed during the treatment. A mean of 500 ml of 5% human albumin solution was administered to each patient.

Whole blood viscosity was measured with a cone plate system (CS-Rheometer Carri Med Ltd., Dorking, UK). Plasma viscosity was determined with the capillary tube plasma viscosimeter (Jung 83). Eythrocyte aggregation was measured with the mini-aggregometer (Myrenne GmbH, Roetgen, Germany) (Kiesewetter 1982). The biochemical parameters, total protein, albumin, fibrinogen, IgG, IgM, IgA, alpha-2-macroglobulin, total cholesterol, triglycerides, LDL, VLDL and HDL were determined using standard procedures as described in detail before (Brunner 1995).

Results

Main parameter of the study was the best corrected visual acuity measured with ETDRS-charts (Lighthouse, Long Island, USA). All parameters were determined one day prior to and one day after therapy. Visual acuity was checked again on follow-up 25 days (range 4–90 days) after therapy. For statistical analysis the Wilcoxon signed rank test was used. P<0.05 was regarded as statistically significant.

No side effects occurred during or after treatment. The rheological parameters, plasma viscosity, whole blood viscosity and erythrocyte were still significantly decreased one day after therapy. The haematocrit of the patients was not affected by treatment. There was a significant reduction of total protein, fibrinogen, IgG, IgM, IgA, alpha-2-macroglobulin, total cholesterol, LDL and HDL. Albumin remained unchanged after therapy. Triglycerides and VLDL were decreased after therapy, but the differences were not statistically significant. The changes of biochemical and rheological parameters are summarized in table I.

The mean visual acuity of all eyes was 0.55 log MAR (SD 0.34) before therapy and changed to 0.41 log MAR 8SD 0.31) after therapy. On follow-up mean visual acuity was still 0.41 log MAR (SD 0.32).

Visual acuity was increased by more than one line in 8/10 eyes. Of these eyes three improved their visual acuity by more than two lines. One of these patients showed an improvement of three lines on the ETDRS-chart. The mean change compared to baseline was 1.4 lines (SD 0.8 lines, p=0.002) 24 hours after therapy and was statistically significant. At follow-up the mean improvement compared to the values prior to therapy was still 1.4 lines (SD 1.0 lines, p=0.002). No patient showed a deterioration of visual acuity after therapy. Changes in the macular region were not detectable by slit-lamp biomicroscopy.

Discussion

The results of this pilot study show that membrane differential filtration is a strong tool to influence blood rheology and is able to alter visual function in patients suffering from diabetic retinopathy.

Diabetic retinopathy is one of the leading causes of blindness in the western world. Approximately 25% of diabetics have some form of retinopathy and 90% of all diabetics will develop retinopathy at some time during their lives. The leading cause of visual impairment in diabetics is the occurrence of macular edema (Federman 1994). There is evidence, that a diffuse damage of the retinal vessels affects their patency and permeability. Subsequently microaneurysms, hemorrhage, focal hard exuilates and diffuse intraretinal edema can be observed in mild nonproliferative diabetic retinopathy and lead to visual impairment.

Haemorheological disturbances might play a role in the impairment of microcirculatory blood flow, and may contribute to the development of microangiopathy in diabetes mellitus. It might also contribute to endothelium dysfunction or injury because an increased shear stress caused by an increased blood viscosity can lead to endothelial injury.

Additionally most investigators found a decreased retinal blood flow in diabetics.

Membrane differential filtration eliminates high molecular weight proteins and lipids and is therefore able to lower rheological parameters like whole blood viscosity, plasma viscosity and erythrocyte aggregation. Also the improvement of the pulsatile ocular blood flow as well as the improvement of retinal circulation time after elimination of high molecular weight proteins and lipids were demonstrated.

In this study it was demonstrated, that these changes led to a short term functional improvement in patients suffering from macular edema.

Lowering of blood viscosity and erythrocyte aggregation may lead to a decreased shear stress to the endothelium and to a decreased postcapillary resistance both mechanisms result in a decreased pressure of fluid in the subretinal space. Also, improvement of endothelial function may decrease fluid pressure in the subretinal space. Even a single session of LDL-apheresis, a treatment, for which membrane differential separation originally was developed, is able to alter endothelial function. These three sequelae of membrane differential filtration may explain the short term effects on visual function in diabetics with diabetic retinopathy and clinically significant to enhance visual function in these patients and may therefore give more insights in the development and pathogenesis of visual impairment in diabetics with macular edema.

It is important to stress that haemorheological therapy is an experimental approach and does not replace laser treatment which is mandatory in diabetic retinopathy. A current study is initiated to investigate the long term effects in patients undergoing repetitive treatment with membrane differential filtration.

Table I shows changes in biochemical and haemorheological parameters 24 hours after membrane differential filtration.

| Parameter | Unit | Before therapy mean/sd | | After therapy mean/SD | | Final % | pW |
|---|---|---|---|---|---|---|---|
| Rheology: | | | | | | | |
| Haematocrit | % | 44.4 | 3.2 | 44.2 | 2.9 | 100 | ns |
| PV | mPa s | 1.37 | 0.13 | 1.19 | 0.11 | 87 | * |
| WBV | mPa s | 4.50 | 0.70 | 3.74 | 0.35 | 83 | * |
| EA | rU | 11.44 | 0.83 | 5.99 | 1.73 | 52 | * |
| Proteins: | | | | | | | |
| Total protein | g/l | 75.3 | 9.6 | 59.0 | 6.90 | 78 | * |
| Albumin | g/l | 44.17 | 2.48 | 44.67 | 5.82 | 101 | ns |
| Fibrinogen | g/l | 3.04 | 0.63 | 1.90 | 0.54 | 63 | * |
| IgG | g/l | 15.05 | 2.07 | 9.97 | 0.95 | 66 | * |
| IgA | g/l | 4.73 | 1.42 | 3.01 | 0.94 | 64 | * |
| IgM | g/l | 2.28 | 2.24 | 1.02 | 0.85 | 45 | * |
| A2M | g/l | 2.41 | 0.64 | 1.35 | 0.50 | 56 | * |
| Lipids: | | | | | | | |
| Triglycerides | mg/dl | 224.0 | 118.3 | 179.7 | 59.6 | 80 | ns |
| Cholesterol | mg/dl | 222.8 | 71.0 | 140.3 | 24.7 | 63 | * |
| VLDL | mg/dl | 29.2 | 21.5 | 24.2 | 8.8 | 83 | ns |
| LDL | mg/dl | 148.3 | 45.0 | 85.2 | 20.3 | 57 | * |
| HDL | mg/dl | 45.3 | 13.7 | 30.8 | 8.5 | 68 | * |

Abbreviations: Final = final value in % of the initial value, pW* = p < 0.05 / ns = not significant according to Wilcoxon signed rank test, sd = standard deviation, PV = plasma viscosity, WBV = whole blood viscosity, EA = erythrocyte aggregation, rU = relative units, A2M = alpha-2-macroglobulin, n = 6 patients

EXAMPLE 3

Clinical improvement in patients suffering from maculopathy after plasma perfusion using a tryptophan polyvinylalcohol adsorber.

Seven men and three woman suffering from maculopathy were treated. Maculopathy is a disorder of the central part of the retina. The degeneration of the retina and the adjacent pigment epithelium was diagnosed using indirect ophthalmoscopy and fluorescein angiography. The main symptom of the disease is the reduction of visual acuity which can be evaluated with standard visual acuity charts. In our study maculopathy developed after uveitis (n=6), high myopia (n=1), uveal effusion syndrome (n=1) and in two cases it was age related. Improvement of visual acuity was expected through an improvement of the microcirculation. The mean age of the patients was 55 (SD 11) years.

The treatments were performed applying a plasma separator (Plasmaflo OP-05) and a tR-350 plasma perfusion column separator (Asahi Medical, Tokyo) and were carried out twice within three days with a one day interval. This treatment schedule was chosen empirically considering to reappearence of the plasma proteins as described below. The container of the column (length 221 mm, diameter 76 mm, weight 600 g) is made of polypropylene. The adsorber material consists of tryptophan bound to a polyvinylalcohol gel and has a volume of 350 ml. The adsorption process is mainly based on hydrophobic interaction chromatography. The blood flow was established from one forearm to the other using peripheral veins.

The flow rates were 70–80 ml/min for whole blood and 15–20 ml/min for plasma. One treatment session took between two and three hours depending on the patients total plasma volume. Anticoagulation consisted of heparin (4000 units) injected as a bolus prior to the therapy and ACD-A citrate (Acidium citrium dextrose formule A) was continuously infused in a ratio of 1:16 during the course of treatment.

Rheological and biochemical parameters were determined one day prior to the first treatment and one day after the second treatment. For the evaluation of the Theological parameters 30 ml EDTA (Ethylenediaminetetraacetic acid) blood was drawn. After the centrifugation and the separation of plasma, whole blood samples were adjusted to haematocrits of 15, 30, 45 and 60% using the patient's own plasma. This technique allows a person to observe changes of these parameters independent from the haematocrits. Then plasma viscosity, whole blood viscosity and erythrocyte aggregation were determined within three hours after venipuncture. Viscosity was measured using a cone-plate system (CS-Rheometer Carri Med Ltd., Dorking, UK) at 37 degrees Celsius. Shear stress was regulated from 0 to 1,414 N/m$^2$ over a period of seven minutes. The viscosity was calculated from 200 single measurements taken over this period. Erythrocyte aggregation was measured applying the Mini-Aggregometer (Myrenne GmbH, Roetgen, Germany).

Biochemical parameters were determined with standard procedures: fibrinogen (turbidimetric determination along with prothrombin time), albumin, IgG, IgM, IgA, alpha-2-macroglobulin (nephelometric, Behring, Marburg), total protein (Biuret), total cholesterol (enzymatic assays, Boehringer-Mannheim).

The best corrected visual acuity was measured by ETDRS (Early Treatment Diabetic Retinopathy Study) or Idemvisus projector charts. Plasma volume was determined according to the method of Dagher and coworkers.

The aim of the study was the reduction of plasma viscosity, standardized whole blood viscosity at haematocrit 45% and standardized erythrocyte aggregation at haematocrit 30%. Statistical evaluation was carried out using the Wilcoxon signed rank test. Evaluation were performed on a personal computer with the statistical software StatView 4.01 (Abacus Concepts Inc.). P<0.05 was regarded as statistically significant. Because of multiple testing a p value<0.017 was mandatory for each evaluation to be regarded as significant. The p value of 0.017 (0.05/3) was chosen because three endpoints were tested and in this case a p value<0.017 is equivalent to a p value<0.05 compared to statistical evaluation of a single parameter.

Results

A mean of 89% (SD 15) of the patients' plasma volume was processed during the adsorption procedure.

Two different patients experienced minor side effects shown as transient hypotonic episodes (RR 90/60 mmHg) and mild hypocalcemia (tingling of the finger tips) controlled by intravenous infusion of 250 ml 5% human albumin and oral calcium administration. The mean serum calcium concentration was not decreased in these cases, in ionized form of calcium was not measured.

Plasma viscosity, standardized whole blood viscosity at haematocrit of 45% and standardized erythrocyte aggregation at haematocrit of 30% measured 24 hours after treatment were shown to be significantly lower as shown in table II.

Table II shows the changes in biochemical and haemorheological parameters

| Parameter | Unit | Before therapy (mean ± sd) | After therapy (mean ± SD) | Red % | pW |
|---|---|---|---|---|---|
| Rheology: | | | | | |
| PV | mPa s | 1.49 ± 0.14 | 1.3 ± 0.12 | 87 | 0.005 |
| Sa_WBV | mPa s | 4.21 ± 0.66 | 3.72 ± 0.38 | 88 | 0.007 |
| Sa_EA | rU | 12.25 ± 2.35 | 7.93 ± 0.75 | 65 | 0.005 |
| Haematocrit | % | 44.7 ± 2.5 | 42.2 ± 4.5 | 94 | 0.06 |
| Proteins: | | | | | |
| TP | g/l | 78 ± 7.63 | 68.7 ± 7.39 | 88 | 0.03 |
| Albumin | g/l | 48.7 ± 10.00 | 46.5 ± 7.96 | 95 | 0.36 |
| IgG | g/l | 14.61 ± 4.51 | 9.53 ± 3.66 | 65 | 0.005 |
| IgA | g/l | 3.87 ± 2.37 | 2.83 ± 1.45 | 73 | 0.007 |
| IgM | g/l | 2.70 ± 2.27 | 1.71 ± 1.49 | 63 | 0.005 |
| Fib | g/l | 3.08 ± 0.89 | 1.53 ± 0.31 | 50 | 0.005 |
| A2M | g/l | 2.15 ± 0.83 | 1.80 ± 0.67 | 84 | 0.02 |
| Chol | g/l | 2.51 ± 0.52 | 2.12 ± 0.38 | 84 | 0.04 |

Abbreviations: Red = reduction to % of the initial value, pW = p value according to Wilcoxon signed rank test, sd = standard deviation, PV = plasma viscosity, Sa_WBV = standardized whole blood viscosity at haematocrit 45%, Sa_EA = erythrocyte aggregation at haematocrit 30%, rU = relative units, TP = total protein, Fib = fibrinogen, A2M = alpha-2-macroglobulin, Chol = total cholesterol, n = 10 (except A2M/n = 7; Chol/n = 9

Figure 3:
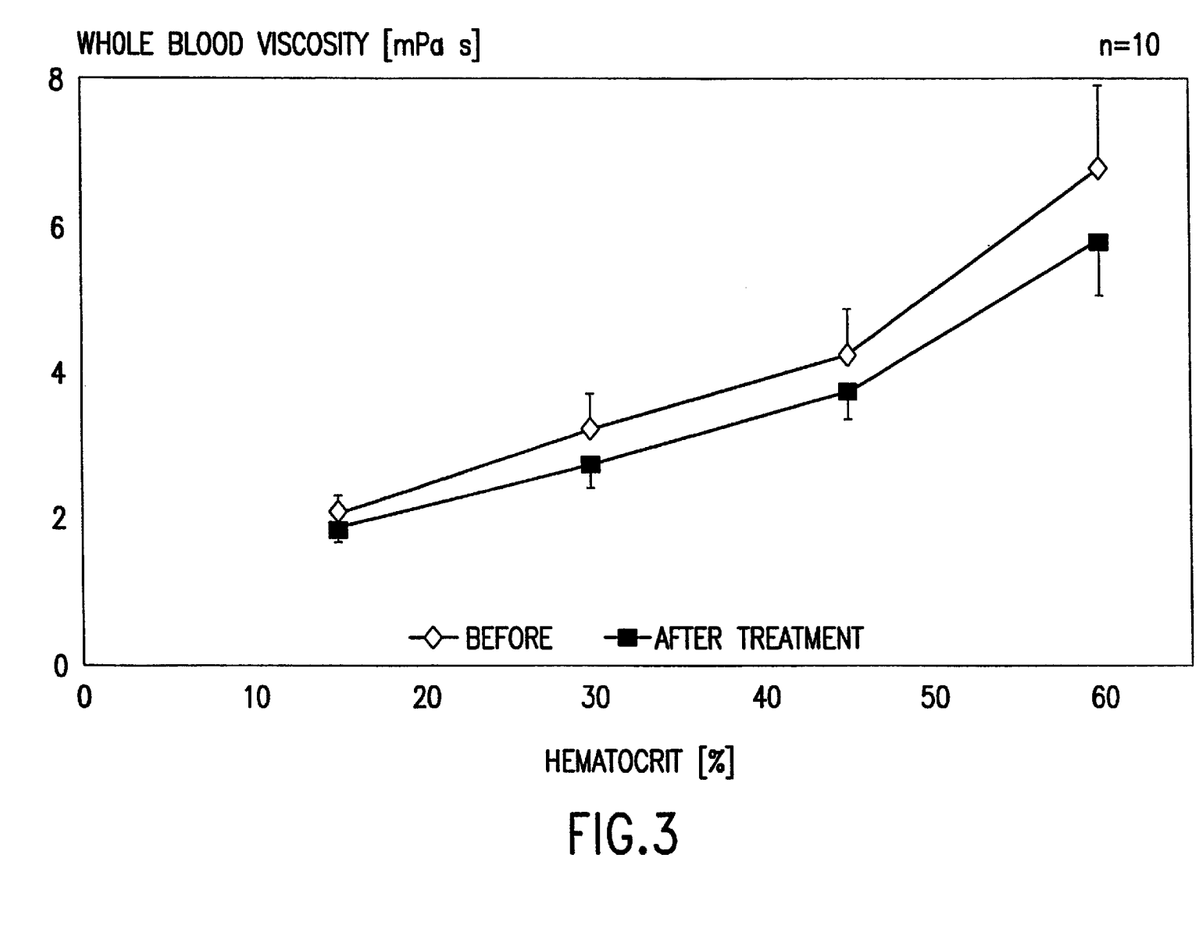
FIG. 3 is a graph that shows whole blood viscosity revealed a non-linear hematocrit dependent rise. A clear reduction after therapy is demonstrated ($p<0.05$).
Figure 4:
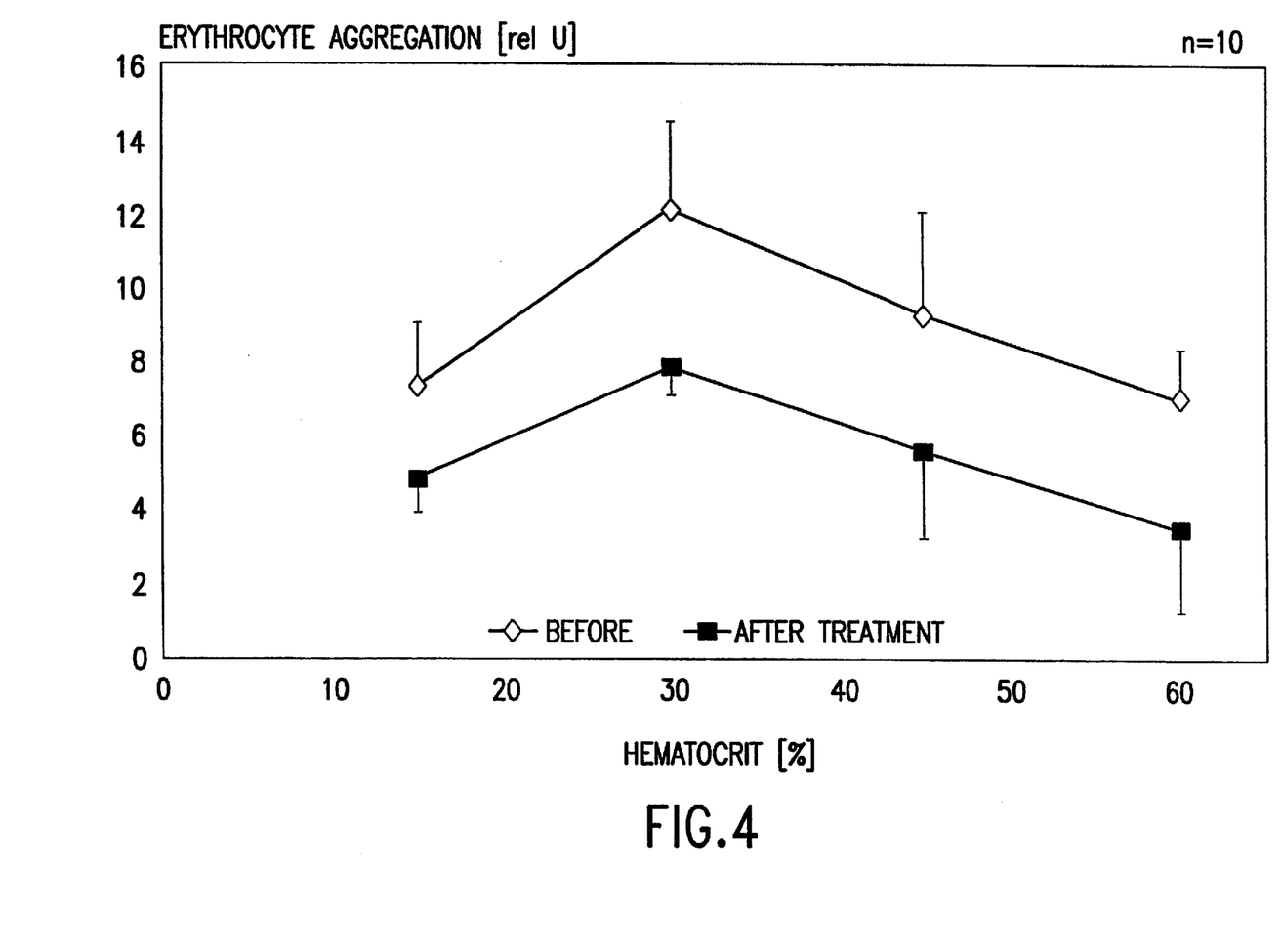
FIG. 4 is a graph that shows the maximum value of erythrocyte aggregation at hematocrit 0.3. A clear reduction after therapy is demonstrated ($p<0.05$).

The graph of the whole blood viscosity revealed a non linear haematocrit dependent rise (FIG. 3), while the graph of the erythrocyte aggregation showed the maximum value at haematocrit 0.3 (FIG. 4). In both diagrams a clear reduction after therapy is demonstrated (p<0.05).

The high molecular weight proteins and lipoproteins such as immunoglobulins, fibrinogen, alpha-2-macroglobulin and total cholesterol were reduced. This resulted in a reduction of total protein while albumin was largely unaffected. The analysis of alpha-2-macroglobulin and total cholesterol values was limited to seven instead of nine patients, as some of the blood samples were lost.

Leucocyte-, erythrocyte and thrombocyte counts and also potassium and sodium values remained unchanged, whereas the calcium level was lowered.

An improvement of visual acuity of at least one line was achieved in six patients 24 hours after therapy (uveitis 4/6, age-related 1/2, uveal effusion 1/1, myopia 0/1) in their better eye. Three of these six revealed a bisection of the visual angle (improvement of three lines or more). These three suffered from uveitis, age-related maculopathy and uveal effusion syndrome.

Discussion

Selective adsorption using the TR-350 column turned out to be an effective extracorporeal treatment to reduce haemorheological determinants like whole blood viscosity, plasma viscosity and erythrocyte aggregation. The effect was shown to be present 24 hours after therapy and was accompanied by clinical improvement. Severe side effects did not occur. They are not typical for adsorption therapy in general and if they occur they appear to depend on the character of the different materials used.

Haemodilution has gained widespread application as an approach of influencing haemorheological parameters. Randomized double blind trials revealed a remarkable influence on whole blood viscosity accompanied by clinical improvement in patients suffering from peripheral arterial disease and retinal vein occlusion.

However, the impact on plasma viscosity and erythrocyte aggregation is still under debate. Using hyper- or isovolemic haemodilution a clear or lasting influence on plasma viscosity could not be demonstrated. The effects remained limited to the time interval between the end of treatment and the measurements performed after the therapy. Changes of plasma viscosity were no more detectable 24 hours later. Long term effects have been described, but the results remained within the ranges of sham-procedures. Similar data were found for the influence on erythrocyte aggregation.

The relation of whole blood viscosity to microcirculation is under debate and should be discussed with caution, as it was demonstrated that the viscosity of whole blood tends towards the values of plasma viscosity in small capillary tubes. Therefore, it is possible that plasma viscosity plays a major role in microcirculatory blood supply. Plasma viscosity and erythrocyte aggregation are determined by the blood level of fibrinogen, high molecular weight proteins like globulins and lipoproteins. Moreover, proteins adhering to the capillary endothelium and therefore interacting with erythrocytes, may contribute to the quantity and quality of the capillary blood flow.

Extracorporeal treatment is able to influence haemorheological parameters by erythrocyte apheresis and the elimination of high molecular weight proteins and lipoproteins. We were able to demonstrate that plasma exchange could be used as a successful treatment of ocular disorders. Because of the potential side effects of plasma exchange a more selective approach to haemorheological therapy using selective adsorption appeared to be attractive and provided for the capacity of the elimination of high molecular weight proteins and lipoproteins and could influence Theological parameters.

A comparison between selective adsorption and plasma exchange, carried out in an earlier study, revealed distinct elimination profiles. A similar decrease of total protein was accompanied by a lower reduction of total cholesterol, alpha-2-macroglobulin and IgM when selective adsorption was used. However, the influence on the rheological parameters plasma viscosity, whole blood viscosity and erythrocyte aggregation was quite similar. Other investigators using another technique for the semiselective removal of high molecular molecules lowered the Theological parameters within the same range. This leads to the conclusion that the removal of the total amount of high molecular weight proteins and lipoproteins and not the selective removal of a single substrate plays the major role for the influence on blood rheology.

Different elimination profiles may lead to different long term effects. A decrease of plasma viscosity with plasma exchange is demonstrated for at least six days whereas the efficacy of plasma precipitation as another selective approach did not last more than 24–48 hours after a single treatment. Our own measurements of the Theological and the biochemical parameters were carried out 24 hours after the second of two treatments. This design permitted to demonstrate significant effect on rheology. However, to which extent long term effects can be achieved remains to be determined.

In conclusion selective adsorption using hydrophobic, interaction chromatography is effective influencing not only biochemical but also rheological parameters and leads to clinical improvement in patients suffering from maculopathies of different origin. According to our preliminary experience these changes seem to be more profound as compared to haemodilution where a clear or lasting influence on plasma viscosity could not be demonstrated as discussed before. It is assumed and currently under investigation that clinical effects may last longer than those observed for haemodilution and extracorporeal plasma differential precipitation. The optimal treatment schedule for lasting effects has to be investigated in further studies.

What is claimed is:

1. A method for the effective therapeutic treatment of ocular diseases which comprises withdrawing blood from a patient, treatment of the blood by plasmapheresis techniques and reinfusing the treated blood.

2. The method according to claim 1, wherein the ocular diseases are selected from the group consisting of age related maculopathy, retinal vein occlusion, diabetic retinopathy, arterial occlusion, uveal effusion syndrome, non-arteritic anterior ischemic optic neuropathy, Stargardt-disease, uveitis, maculopathy of different origin.

3. The method according to claim 1, wherein the plasmapheresis technique is selected from the group consisting of blood cell plasma separation, plasma differential separation, plasma differential precipitation, plasma differential adsorption, plasma differential filtration.

* * * * *